United States Patent
Baker

(10) Patent No.: US 10,905,376 B2
(45) Date of Patent: Feb. 2, 2021

(54) PHYSICAL PARAMETER MEASURING

(71) Applicant: Welch Allyn, Inc., Skaneateles Falls, NY (US)

(72) Inventor: Steven D. Baker, Beaverton, OR (US)

(73) Assignee: Welch Allyn, Inc., Skaneateles Falls, NY (US)

(*) Notice: Subject to any disclaimer, the term of this patent is extended or adjusted under 35 U.S.C. 154(b) by 184 days.

(21) Appl. No.: 15/649,769

(22) Filed: Jul. 14, 2017

(65) Prior Publication Data

US 2019/0015048 A1  Jan. 17, 2019

(51) Int. Cl.
*A61B 5/00* (2006.01)
*G06F 19/00* (2018.01)
(Continued)

(52) U.S. Cl.
CPC .......... *A61B 5/6833* (2013.01); *A61B 5/0002* (2013.01); *G06F 19/3418* (2013.01); *G16H 20/00* (2018.01); *G16H 40/63* (2018.01); *G16H 40/67* (2018.01); *A61B 5/021* (2013.01); *A61B 5/024* (2013.01); *A61B 5/0402* (2013.01);
(Continued)

(58) Field of Classification Search
USPC .......................... 600/300–301, 391; 705/2–3
See application file for complete search history.

(56) References Cited

U.S. PATENT DOCUMENTS 6,441,747 B1 * 8/2002 Khair .................. A61B 5/0006
128/903
6,454,708 B1 * 9/2002 Ferguson ............. A61B 5/6831
600/300

(Continued)

FOREIGN PATENT DOCUMENTS

CN   203848949 U    9/2014
CN   104248837 A   12/2014
EP     2843848 A1   3/2015

OTHER PUBLICATIONS

Doukas et al., "Managing Wearable Sensor Data Through Cloud Computing," 2011 IEEE Third International Conference on Cloud Computing Technology and Science (CloudCom): 440-445, Nov. 29, 2011.

(Continued)

*Primary Examiner* — Michael W Kahelin
*Assistant Examiner* — Shirley X Jian
(74) *Attorney, Agent, or Firm* — Merchant & Gould P.C.

(57) ABSTRACT

A system for detecting one or more physical assessment parameters of a subject includes a sensing patch and a processor. The sensing patch is configured to sense signals from the subject corresponding to one or more physical assessment parameters, reduce sensed parameter data corresponding to the sensed signals, and transmit the sensed parameter data. The sensing patch also includes at least one adjustable sensing patch parameter. The processor is separate from the sensing patch and configured to receive the sensed parameter data from the sensing patch and transmit (Continued)

a command to the sensing patch. The sensing patch is configured to perform different amounts of data reduction on the sensed parameter data before transmitting the sensed parameter data to the processor. These different amounts of data reduction are determined at least in part by one or more system parameters.

11 Claims, 7 Drawing Sheets

(51) Int. Cl.
<table>
<tr><td>G16H 40/63</td><td>(2018.01)</td></tr>
<tr><td>G16H 20/00</td><td>(2018.01)</td></tr>
<tr><td>G16H 40/67</td><td>(2018.01)</td></tr>
<tr><td>A61B 5/11</td><td>(2006.01)</td></tr>
<tr><td>A61B 5/021</td><td>(2006.01)</td></tr>
<tr><td>A61B 5/024</td><td>(2006.01)</td></tr>
<tr><td>A61B 5/0402</td><td>(2006.01)</td></tr>
<tr><td>A61B 5/08</td><td>(2006.01)</td></tr>
<tr><td>G16H 80/00</td><td>(2018.01)</td></tr>
</table>

(52) U.S. Cl.
CPC .......... *A61B 5/0816* (2013.01); *A61B 5/1116* (2013.01); *A61B 5/1123* (2013.01); *A61B 5/721* (2013.01); *A61B 2560/0209* (2013.01); *A61B 2562/08* (2013.01); *G16H 80/00* (2018.01)

(56) References Cited

U.S. PATENT DOCUMENTS

<table>
<tr><td>6,675,130</td><td>B2</td><td>1/2004</td><td>Kanevsky et al.</td><td></td></tr>
<tr><td>7,324,848</td><td>B1*</td><td>1/2008</td><td>Turcott</td><td>A61B 5/14551<br>607/17</td></tr>
<tr><td>7,382,247</td><td>B2*</td><td>6/2008</td><td>Welch</td><td>A61B 5/0024<br>340/539.12</td></tr>
<tr><td>7,705,725</td><td>B2</td><td>4/2010</td><td>Matsen et al.</td><td></td></tr>
<tr><td>7,844,687</td><td>B1</td><td>11/2010</td><td>Gelvin et al.</td><td></td></tr>
<tr><td>9,165,846</td><td>B2</td><td>10/2015</td><td>Renken</td><td></td></tr>
<tr><td>9,395,792</td><td>B1*</td><td>7/2016</td><td>Kahn</td><td>G06F 1/3231</td></tr>
<tr><td>10,194,802</td><td>B2*</td><td>2/2019</td><td>Windolf</td><td>A61B 5/0031</td></tr>
<tr><td>2002/0013551</td><td>A1*</td><td>1/2002</td><td>Zaitsu</td><td>A61M 5/1413<br>604/151</td></tr>
<tr><td>2005/0090756</td><td>A1*</td><td>4/2005</td><td>Wolf</td><td>A61N 1/08<br>600/546</td></tr>
<tr><td>2005/0113647</td><td>A1*</td><td>5/2005</td><td>Lee</td><td>A61B 5/0031<br>600/300</td></tr>
<tr><td>2005/0206518</td><td>A1*</td><td>9/2005</td><td>Welch</td><td>A61B 5/0404<br>340/539.12</td></tr>
<tr><td>2005/0261559</td><td>A1*</td><td>11/2005</td><td>Mumford</td><td>A61B 5/0002<br>600/300</td></tr>
<tr><td>2006/0242285</td><td>A1</td><td>10/2006</td><td>Moriwaki</td><td></td></tr>
<tr><td>2009/0240193</td><td>A1*</td><td>9/2009</td><td>Mensinger</td><td>A61B 5/7445<br>604/66</td></tr>
<tr><td>2009/0261987</td><td>A1</td><td>10/2009</td><td>Sun</td><td></td></tr>
<tr><td>2010/0223080</td><td>A1</td><td>9/2010</td><td>Basir et al.</td><td></td></tr>
<tr><td>2011/0251469</td><td>A1</td><td>10/2011</td><td>Varadan</td><td></td></tr>
<tr><td>2012/0089370</td><td>A1*</td><td>4/2012</td><td>Chebbo</td><td>A61B 5/0002<br>702/188</td></tr>
<tr><td>2012/0165616</td><td>A1*</td><td>6/2012</td><td>Geva</td><td>A61B 5/0022<br>600/300</td></tr>
<tr><td>2015/0164377</td><td>A1*</td><td>6/2015</td><td>Nathan</td><td>A61B 5/6802<br>600/595</td></tr>
<tr><td>2017/0086709</td><td>A1*</td><td>3/2017</td><td>Khine</td><td>A61B 5/6833</td></tr>
<tr><td>2017/0164291</td><td>A1*</td><td>6/2017</td><td>Ludwig</td><td>H04W 52/0254</td></tr>
<tr><td>2018/0129786</td><td>A1*</td><td>5/2018</td><td>Khine</td><td>G16H 50/20</td></tr>
</table>

OTHER PUBLICATIONS

Zaslaysky et al., "Sensing as a Service and Big Data," Proceedings of the International Conference on Advances in Cloud Computing (ACC): pp. 21-29, Jul. 2012.

Liu et al., "Energy Efficient GPS Sensing With Cloud Offloading," SenSys '12—Proceedings of the 10th ACM Conference on Embedded Network Sensor Systems: pp. 85-98, Nov. 6, 2006.

Min et al., "Low-power Wireless Sensor Networks," Fourteenth International Conference on VLSI Design: pp. 205-210, 2001.

\* cited by examiner

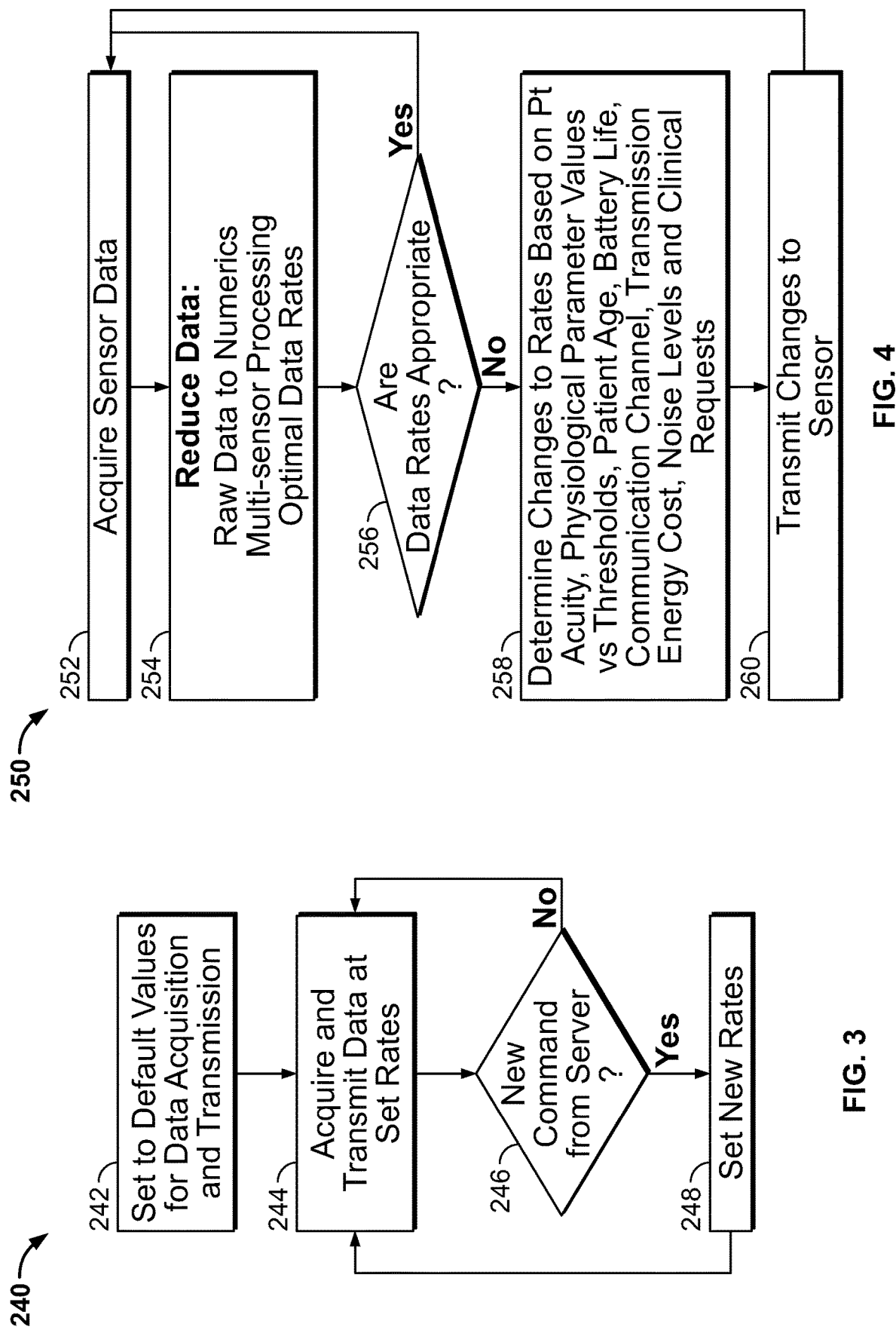

PHYSICAL PARAMETER MEASURING

BACKGROUND

The use of wearable body sensors that monitor physiological parameters, such as vital signs, is becoming very common. For example, wearable body sensors may be used to monitor heart rate, temperature, respiratory rate, blood oxygen concentration and/or any of a large number of other parameters. Oftentimes, especially in a healthcare setting, it may be advantageous to have sensors that are small in size but also allow for a relatively long run time. The small size typically enhances comfort and ease of application of the sensors to the patient's skin or clothing, and the long run time allows for continuous monitoring over a period of many hours or even days, for example the length of a patient's hospital stay in some cases.

The challenge with providing a sensor that is both small and also allows for a long run time is that these two characteristics typically conflict with one another. In other words, sensors that have long run times may have to be larger, for example to allow for sufficient processing power on the sensor. Due to this conflict, wearable sensors are often designed to monitor only one physiological parameter. This allows them to be small and have a long run time.

SUMMARY

In general terms, this disclosure is directed to a system and method for monitoring physical assessment parameters (or "physiological parameters," which terms are used synonymously herein), using one or more wearable sensors and a processor located separate from (or "off of") the sensors. In one possible configuration and by non-limiting example, the system includes a patch sensor and a processor. The patch sensor is configured to attach to a person's body or clothing and to wirelessly transmit sensed data to the processor, which may be located, for example, on a server or in the cloud. The processor is configured to process the data it receives from the sensor and, in some embodiments, to provide instructions to the sensor. Various aspects are described in this disclosure, which include, but are not limited to, the following aspects.

In one aspect of the disclosure, a system for detecting one or more physical assessment parameters of a subject may include a sensing patch and a processor. The sensing patch is configured to sense signals from the subject corresponding to the one or more physical assessment parameters, reduce sensed parameter data corresponding to the sensed signals, and transmit the sensed parameter data. Also, the sensing patch includes at least one adjustable sensing patch parameter. The processor is separate from the sensing patch and is configured to receive the sensed parameter data from the sensing patch and transmit a command to the sensing patch. The sensing patch is configured to perform different amounts of data reduction on the sensed parameter data before transmitting the sensed parameter data to the processor. The different amounts of data reduction are determined at least in part by one or more system parameters corresponding to a function of the system. The sensing patch and/or the processor are configured to determine the different amounts of data reduction, based at least in part on the at least one system parameter.

Examples of the adjustable sensing patch parameter include, but are not limited to, a data reduction rate, a rate at which the sensing patch senses signals from the subject, a monitored vital sign, a data uplink interval and a vital signs interval. In some embodiments, the different amounts of data reduction are further determined, at least in part, by a state of the subject. For example, the state of the subject may be defined at least in part by one or more criteria, such as but not limited to an acuity of the subject, an age of the subject and an input from a healthcare worker that describes the state of the subject. Examples of system parameters include, but are not limited to, a battery level of the sensing patch, an energy cost of transmitting sensed parameter data from the sensing patch to the processor, a noise level, a link rate for linking the sensing patch with the processor and a link reliability for linking the sensing patch with the processor.

In some embodiments, the system also includes a bridge configured to receive the data from the sensing patch and transmit the data to the processor. In some embodiments, the command transmitted from the processor to the sensing patch includes an amount of data reduction to be performed by the sensing patch, and the sensing patch is configured to receive and react to the command. Examples of physical assessment parameters include, but are not limited to, a heart rate, a respiratory rate, a blood pressure, a temperature, a blood oxygen content, blood chemistry, pupil activity, galvanic skin response, weight, oxygen saturation, photoplethysmograph activity, an electrocardiogram signal, an electroencephalogram signal, and a movement of the subject.

In another aspect of the present disclosure, a method for detecting a physical assessment parameter of a subject first involves determining a first physiological assessment parameter to sense with a sensor attached to the subject, determining when to sense the first physiological assessment parameter with the sensor, and sensing the first physiological assessment parameter with the sensor to provide first sensed parameter data. The method then involves transmitting the first sensed parameter data from the sensor to a processor, determining with the processor that additional processing of the first sensed parameter data is needed, and processing the first sensed parameter data with the processor. Finally, the method involves providing the processed first sensed parameter data to a user.

In some embodiments, the method may further involve repeating the steps for a second physiological assessment parameter. In some embodiments, the same sensor is used for both parameters, while in other embodiments a second sensor may be used for the second parameter. In some embodiments, the method further involves transmitting a command from the processor to the sensing patch, receiving the command at the sensing patch and adjusting a setting of the sensing patch in response to the command. For example, the setting may be a rate of data acquisition by the sensing patch, a rate of data transmission from the sensing patch to the processor or the like. In some embodiments, the method may also include determining, with the processor, that the command will be transmitted, based at least in part on an input selected from the group consisting of an acuity of the subject, an age of the subject, an instruction from a healthcare worker, a battery level of the sensing patch, an energy cost of transmitting data from the sensing patch to the processor, a noise level, a link rate for linking the sensing patch with the processor and a link reliability for linking the sensing patch with the processor.

In some embodiments, the first sensed parameter data is transmitted to the processor via a bridge computer device wirelessly coupled with the sensing patch via a short range radio interface and with the processor via a network interface. Optionally, the method may also include performing initial processing of the first sensed parameter data with the sensing patch before transmitting the first sensed parameter data to the processor. In some embodiments, performing initial processing of the first sensed parameter data may involve reducing the first sensed parameter data. In various embodiments, providing the first processed data to the user involves transmitting the first processed data through a network to an electronic health record, a smart phone, a computer tablet device, a laptop computer, a desktop computer and/or a ward dashboard in a healthcare facility.

In yet another aspect, a system for analyzing patient vital signs includes a database, a server, a set of clinically validated algorithms, and at least one patient-worn physiological measurement device. The database includes physical assessment parameter data and clinical results for patients. The server is configured to analyze the physical assessment parameter data and clinical results to determine, based on the clinically validated algorithms, commands for the patient-worn physiological measurements device.

In some embodiments, the data analysis by the server further provides guidance to the clinician for patient care. For example, the guidance may be based on statistically likely outcomes based on comparison of the state of the current patient with the outcomes or diagnoses of prior patients with similar states. Optionally, the system may also include test algorithms, which include updates based on additional physical assessment parameter data and clinical outcomes compared with the clinically validated algorithms. In some embodiments, the data analysis by the server includes performance testing of the test algorithms engine and the clinically validated algorithms using patient data and clinical results acquired after the test rule the test algorithms were created. In some embodiments, the test algorithms replace the clinically validated algorithms when the statistical match of the guidance from the test algorithms with actual outcomes is superior to the statistical match of the guidance from the clinically validated algorithms.

These and other aspects and embodiments are described in further detail below, in relation to the attached drawing figures.

BRIEF DESCRIPTION OF THE DRAWINGS

FIG. 3 schematically illustrates a portion of an example method for wirelessly sensing one or more physical assessment parameters of a subject.

FIG. 4 schematically illustrates another portion of the example method of FIG. 3 for wirelessly sensing one or more physical assessment parameters of a subject.

DETAILED DESCRIPTION

Figure 1:
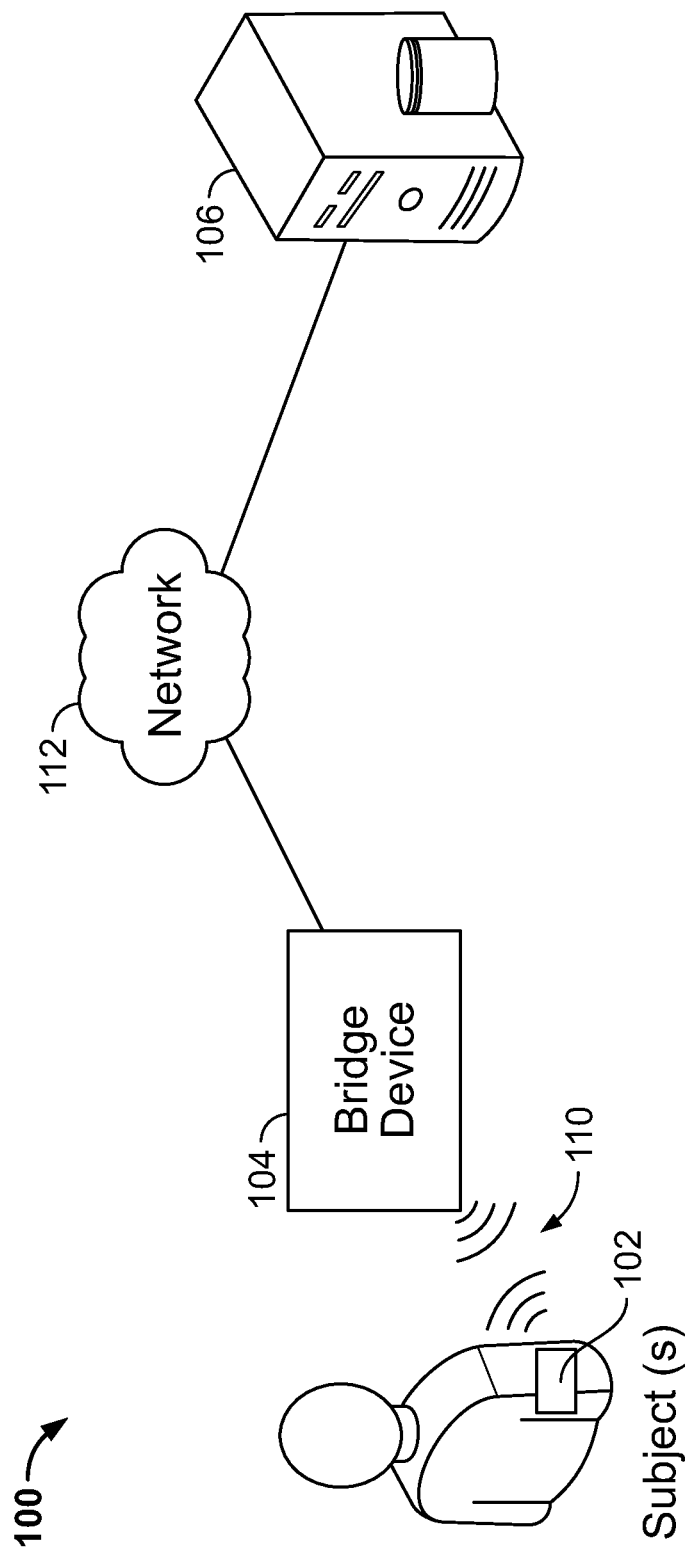
FIG. 1 schematically illustrates an example system for wirelessly sensing one or more physical assessment parameters of a subject.

Various embodiments will be described in detail with reference to the drawings, wherein like reference numerals represent like parts and assemblies throughout the several views.

In general, a physical assessment parameter sensing system in accordance with an exemplary embodiment of the present disclosure includes a sensing patch and a processor located separate and apart from the sensing patch. The sensing patch may include a first layer with an adhesive, a circuit fixed relative to the first layer and including a sensor unit for detecting one or more physical assessment parameters of the subject, a sensor processor, and an antenna electrically connected to the circuit and configured to receive and transmit a radio frequency signal. The processor is configured to communicate wirelessly with the sensing patch and receive the physical assessment parameter(s) from the sensing patch. The sensor processor may provide a dynamic amount of data analysis and data reduction, based on available system resources. System resources and system state include aspects of the data acquisition, transmission, and analysis systems, and they may include, for example, for each component in the system: processing power, available memory, battery life, on-time, duty cycle, sampling rates, sensors, communication bandwidth, signal-to-noise ratio, data error rate, time to next data reading, and/or time to next data transmission. Data reduction is the process of analyzing raw data to create a meaningful/actionable result. For example, in RADAR, data reduction transforms received RF signals into range, direction and velocity of the target relative to the RADAR.

FIG. 1 schematically illustrates an example system 100 for wirelessly sensing one or more physical assessment parameters of a subject S. The system 100 can include a physical assessment parameter sensing device 102, a bridge device 104, and a data management system 106. The physical assessment parameter sensing device 102 can communicate with the bridge device 104 via a wireless communication link 110. The bridge device 104 can communicate with the data management system 106 via a data communication network 112. Dynamic, distributed processing between the sensing device 102, the bridge device 104 and the data management system 106 may be supported, and the processing load of each device depends on system resources, system state and patient state. Patient state may include, for example, patient acuity, age, history, diagnosis, prescriptions, recent medications, prior vital signs values, gender, race, time since medical events such as surgery and intubation, time since last clinical interaction, and/or scaled patient performance, such as pain level, AVPU, APGAR, and Glasgow coma score.

The physical assessment parameter sensing device 102 is worn or carried by the subject S. In some examples, the sensing device 102 includes a physical assessment parameter sensing patch, as described below. In this document, therefore, the sensing device 102 is also referred to as a physical assessment parameter sensing patch 102.

In some examples, the sensing device 102 is removably attached to a portion of the subject's body or the subject's skin. The sensing device 102 can be worn on different locations of the subject body, such as the forehead, torso, neck, arm, leg, or other on-body locations, for different measurements. In other examples, the sensing device 102 is ingested or implanted in the subject's body. The sensing device 102 can be attached to, or implanted in, the subject S by a healthcare practitioner when the healthcare practitioner sees the subject S. In other examples, the subject S can wear or attach the sensing device 102 on his or her own.

The sensing device 102 operates to detect one or more physical assessment parameters of the subject S. (The subject S may also be referred to herein as a "patient" or "person.") The sensing device 102 is configured to detect one or more physical assessment parameters. In some examples, the sensing device 102 includes one sensor unit 132 (FIG. 5) to measure the same type of physical assessment parameters. In other examples, the sensing device 102 includes multiple sensor units 132 of different types, capable of detecting different kinds of physical assessment parameters. The sensing patch 102 transmits signals to the bridge device 104 via the wireless communication link 110.

Physical assessment parameters can include vital signs, physiological measurements, and biological measurements, which can be detected from various portions of the subject's body. For example, physical assessment parameters include measurements of the body's basic functions, which are useful in detecting or monitoring medical problems. Examples of physical assessment parameters include body temperature, pulse rate (i.e., heart rate), respiratory rate (i.e., breathing rate), blood pressure, electrocardiogram (ECG) signals, electroencephalogram (EEG) signals, blood oxygen content, blood chemistry, pupil diameter, scales such as APGAR, AVPU, pain or the Glasgow coma score, and many more. Body temperature can be taken in various manners, such as orally, rectally, by ear, by skin (including infrared imaging) detectors, or the like. In addition to heart rate, or the number of times the heart beats per minute, the sensing patch 102 may also sense a heart rhythm and/or strength of the pulse and pulse characteristics, such as "thready." The pulse can be taken on different body parts where the arteries are located, such as on the side of the neck, on the side of the elbow, or at the wrist. The respiration rate is the number of breaths a person takes per minute and is used to note whether the person has any difficulty breathing. Breathing issues such as rales, rhonchi, stridor, wheezing or apnea may be detected. Blood pressure is the force of the pushing against the artery walls. There may be other vital signs, such as pain, cyanosis, capillary refill time, alertness, Glasgow coma scale, pulse oximetry, blood glucose level, end-tidal $CO_2$, functional status, shortness of breath, and gait speed.

In some examples, the sensing patch 102 is configured without an independent power source, such as a battery, to supply power to the components of the sensing patch 102. In this configuration, the sensing patch 102 can be activated by the bridge device 104 when the bridge device 104 comes close to the sensing patch 102 within a predetermined activation or read range and power is supplied to the sensing patch 102 from the bridge device 104. In other examples, the sensing patch 102 includes its own power supply. An example of the sensing device 102 is described and illustrated in more detail with reference to FIGS. 5-11.

With continued reference to FIG. 1, the bridge device 104 operates to communicate with the sensing device 102 attached to the subject S. The bridge device 104 can receive signals from the sensing patch 102 via the wireless communication link 110. In some examples, the bridge device 104 is operable to present the data transmitted from the sensing patch 102 thereon. For example, the bridge device 104 may include a display screen and operate to present the transmitted data on the screen in a visible format. In some embodiments, the bridge device 104 can output the data in an audible format, and/or provide an alert in visible and/or audible manners. The bridge device 104 can also be in communication with the data management system 106 via the network 112. The data management system 106 may provide analysis and reduction of the received data.

The bridge device 104 can be used by a guardian and/or a healthcare practitioner to monitor the measurement of the sensing device 102. The guardian is a person or a group of people who is interested in the health conditions of the subject S. Examples of the guardian include a parent of the subject S, a family member of the subject S, a caregiver of the subject S, a primary physician of the subject S, and any other interested parties. The healthcare practitioner is a person who provides healthcare service to the subject S. Examples of healthcare practitioners P include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services. The healthcare practitioner can be an institution, company, business, and/or entity. In other examples, the bridge device 104 can be operated by the subject S him or herself. The guardian and/or healthcare practitioner may also monitor the measurement of the sensing device 102 via a separate computing device (not shown) that has a network 112 connection to data management system 106.

The bridge device 104 can be of various types. In some examples, the bridge device 104 is a computing device dedicated for particular sensing devices 102. In other examples, other consumer level computing devices can be used for the bridge device 104. Such computing devices can include a mobile computing device, such as a smartphone, (e.g., an iPhone, an Android operating phone, a Blackberry, a Window operating phone, etc.); a tablet computer (e.g., an iPad), and a personal digital assistant (PDA). The bridge device 104 can include a desktop computer, a laptop computer, and/or any other suitable devices operable to send and receive signals, store and retrieve data, and/or execute modules.

The bridge device 104 generally supports both a network interface and a short range communication interface, for example an RF, acoustic (including subsonic and ultrasonic) or optical (including IR, UV, and visible) interface. Smart phones may act as the bridge device 104, as may any of a number of different types of radio chipsets that support BT Classic, BT LE, cellular (including IoT) and Wi-Fi. An example is the Newmar® Radio, available from Welch Allyn Inc., Skaneateles Falls, N.Y. The patch 102 may support IPV6 and provide an IP endpoint. In some embodiments, the bridge device 104 may include a processor that can support applications, including analysis and reduction of sensor data. This data analysis may be performed fully on the bridge device 104 or only in part (distributed processing). For example, the bridge device 104 may compute one key numeric value, such as heart rate, and use the heart rate data to make decisions, such as whether or not to forward an entire data packet to the data management system 106 or to change the data sampling rate of the sensing patch 102. Alternately, the bridge device 104 may simply forward the data to the data management system 106 without performing any processing or analysis of the data.

In some examples, the bridge device 104 is configured as a portable reader. Such a portable bridge device 104 can be configured as an independent handheld device, or as a device that is connected to a movable clinical data station or equipment. As described herein, for home care, the bridge device 104 can be various consumer mobile devices as described above. In other examples, the bridge device 104 is mounted to a structure or device that the subject S periodically or continuously uses. For example, the bridge device 104 is mounted to the sides or side rails of a hospital or homecare bed for a patient, such that the bridge device 104 remains within, or easily comes into, a read range of the sensing patch 102 attached to the patient's body. In yet other examples, the bridge device 104 is incorporated into, or used with, other monitoring systems, such as Connex® Vital Signs Monitor (CVSM), available from Welch Allyn Inc., Skaneateles Falls, N.Y. An example of the bridge device 104 is described in more detail with reference to FIG. 12.

Referring still to FIG. 1, the data management system 106 operates to manage the subject's health conditions and other information. The subject data management system 106 can be operated by the healthcare practitioner and/or a healthcare service provider, such as a hospital or clinic. Some embodiments of the data management system 106 are configured to receive measurement data (and other data associated with the subject S) from the bridge device 104, and analyze the data for various purposes. In some embodiments, the data management system 106 operates to provide information that can be used to assist the guardian and/or the healthcare practitioner to provide suitable healthcare to the subject S. In some examples, the data management system 106 includes a computing device as described in FIG. 12. Examples of the data management system 106 include Connex® data management systems available from Welch Allyn Inc., Skaneateles Falls, N.Y.

As illustrated in FIG. 1, the wireless communication link 110 is established between the sensing patch 102 and the bridge device 104. The data collected by the sensing patch 102 are wirelessly transmitted to the bridge device 104 via the wireless communication link 110. The wireless communication link 110 can be established as short range wireless communication, such as radio frequency identification (RFID) communication, near field communication (NFC), Bluetooth communication, or Wi-Fi communication. Low power wide area (LPWA) network solutions, such as a cellular IoT module, may also be used, for example the Sierra Wireless LTE-M module and the Telit ME910 and ME866. The functionality of the bridge device 104 may be included in sensor 102.

In some examples, the bridge device 104 is configured as an active RFID reader and capable of communicating with the sensing patch 102, which correspondingly includes a RFID device (e.g., a RFID tag). When the bridge device 104 is brought close enough to the sensing patch 102 attached to the subject S, a short-range power and RF communication is established between the sensing patch 102 and the bridge device 104 via electromagnetic fields so that query, authorization/authentication, and/or data interchange processes are performed between the sensing patch 102 and the bridge device 104.

In other examples, the bridge device 104 includes a NFC interface for establishing radio communication with the sensing patch 102 by bringing the bridge device 104 into proximity to the sensing patch 102 or touching the bridge device 104 with the sensing patch 102. The NFC interface can be configured in a way known in the art. The sensing device 102 is correspondingly configured to communicate with the NFC interface of the bridge device 104. As such, the bridge device 104 operates as an NFC reader and the sensing device 102 functions as an NFC tag. Because the patch 102 is on the subject S, capacitive communication may be used to communicate data via the patient's body. Similarly, near-field magnetic induction and other short-range wireless communication may be used.

In yet other examples, the bridge device 104 includes a Bluetooth communication interface to establish Bluetooth wireless connection with the sensing device 102. The Bluetooth communication interface can be configured in a way known in the art. The sensing device 102 is also configured to be capable of establish Bluetooth communication with the bridge device 104. As such, the sensing device 102 and the bridge device 104 can be correspondingly configured to transmit data via low-power radio waves. NFC, capacitive, inductive and/or acoustic methods may be used to transmit out-of-band (OOB) information to a receiver device, such as the bridge device 104.

In yet other examples, the bridge device 104 includes a Wi-Fi communication interface to establish Wi-Fi connection with the sensing device 102. The Wi-Fi communication interface can be designed in a way known in the art. The sensing device 102 is also configured to communicate with the Wi-Fi communication interface of the bridge device 104. As such, the sensing device 102 and the bridge device 104 can be correspondingly configured to transmit data via radio waves. By way of non-limiting example, standards-based RF systems can be deployed in accordance with IEEE 802.11 (Wireless LAN), IEEE 802.15.4 (Low-Rate wireless PAN, such as ZigBee, WirelessHART, MiWi, infrared data communication, Z-Wave, ANT+, or other suitable protocols), IEEE 802.22 (Wireless Regional Area Network), or other standard. In some embodiments, Wi-Fi connection can be alternatively established if other connections (e.g., RFID, NFC, cellular and Bluetooth) are not established.

With continued reference to FIG. 1, the data communication network 112 communicates digital data between one or more computing devices, such as among the bridge device 104 and the data management system 106. Examples of the network 112 include a local area network and a wide area network, such as the Internet. In some embodiments, the network 112 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. Capacitive and inductive coupling are other forms of wireless communication. A wireless communication system typically includes an optical or RF transmitter for transmitting optical or RF signals, and an optical or RF receiver for receiving optical or RF signals. Examples of wireless communication systems include Wi-Fi communication devices (such as using wireless routers or wireless access points), cellular communication devices (such as using one or more cellular base stations), and other wireless communication devices.

As such, since the sensing device 102 and the bridge device 104 communicate with each other via the wireless communication link 110, the system 100 allows for conveniently measuring physical assessment parameters without requiring the patient's involvement. For example, when a patient is asleep, a user can simply bring the bridge device 104 close to the sensing device 102 to activate the sensing device 102 and/or receive the measurements from the sensing device 102 without waking the patient.

In some embodiments, data reduction is performed locally, on the sensing device 102. In other embodiments, the sensing device 102 transmits raw data, and complex processing (data reduction) is completed elsewhere, possibly using distributed computation. In some of these embodiments, the sensing device 102 may be a multi-parameter wearable sensor, meaning that it is capable of measuring multiple different patient parameters, such as blood pressure, heart rate, blood oxygen saturation, etc. In some embodiments, such a multi-parameter wearable sensor may transmit raw data for data reduction elsewhere. In some embodiments, the system 100 is configured to determine when to process data locally (at the sensing device 102) and when to process it elsewhere, based on inputs such as but not limited to patient acuity, battery level, energy cost to transmit data, link rate and link reliability. In some embodiments, the sensing device 102 and the system 100 support cloud computing and data aggregation to support multi-sensor analysis. In some embodiments, the system 100 is configured to dynamically adjust the amount of data gathered and the amount of data transmitted as a function of inputs such as patient acuity, noise levels, battery life, link quality and the like. In some embodiments, the sensing device 102 may provide data that may be aggregated with data from a gateway device that bridges from wireless sensors on a BAN and provides for addition of other patient parameters.

Figure 2:
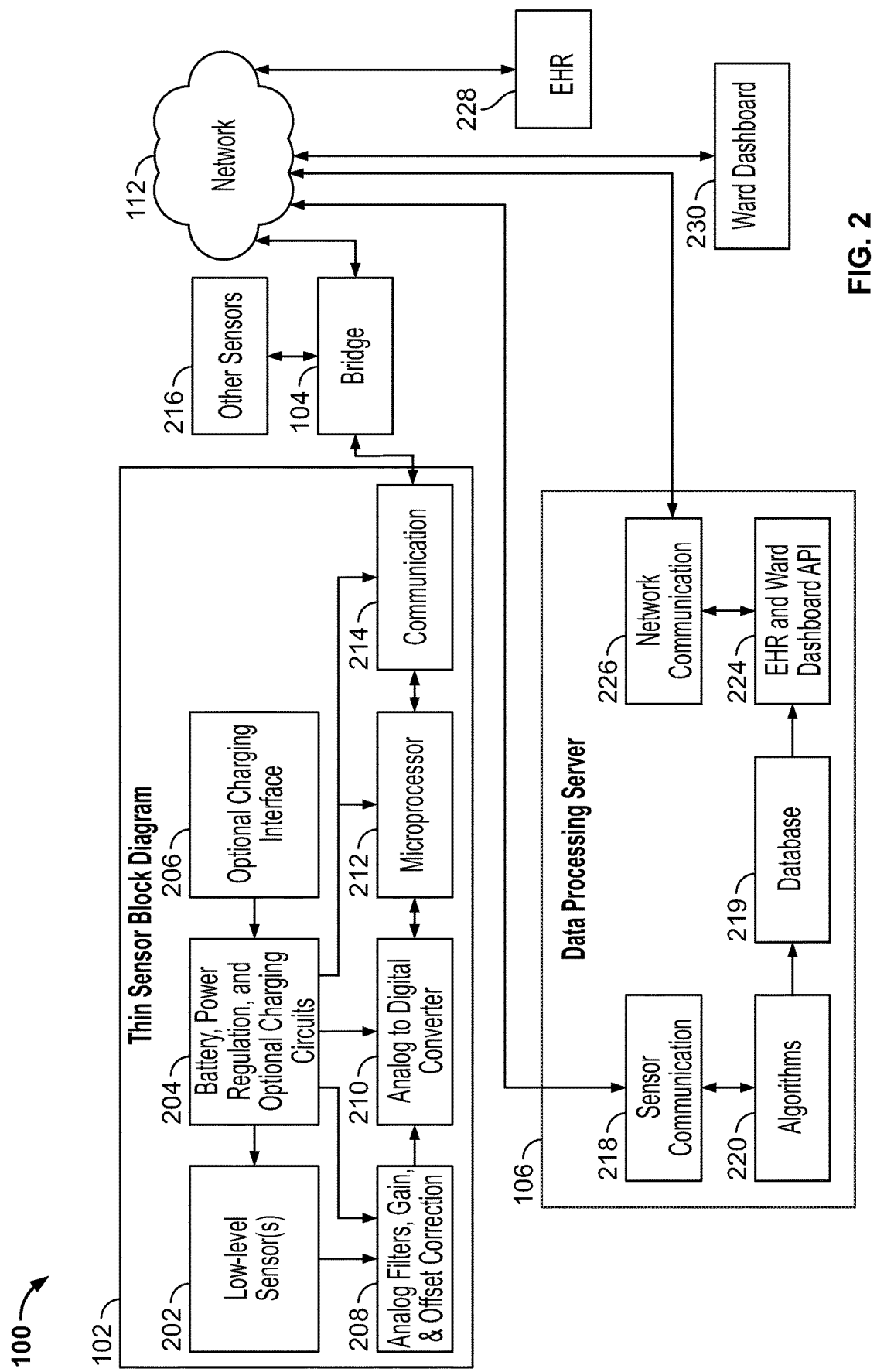
FIG. 2 is a more detailed schematic illustration of the system of FIG. 1 for wirelessly sensing one or more physical assessment parameters of a subject.

FIG. 2 is a more detailed schematic representation of the system 100. Again, the system 100 includes the sensing patch 102, the bridge device 104, the network 112 and the data management system 106, which in this embodiment is represented as a data processing server 106. The sensor patch 102 includes one or more low-level sensors 202, for sensing one or more physical assessment parameters. It may also include battery, power regulation and/or charging circuits 204 and an optional charging interface 206. The sensing patch 102 may also include analog filter, gain and offset correction module 208, an analog to digital converter 210, a microprocessor 212 and a communication module 214, which allows the sensing patch 102 to communicate with the bridge device 104. According to various embodiments, one or more additional sensing patches 216 may also communicate with the bridge device 104.

The data processing server 106 may include a sensor communication module 218, an algorithm module 220, an electronic health records (EHR) and ward dashboard application program interface (API) module 224 and a network communication module 226 and a database 219. The database 219 may share data with the database in the EHR. The algorithm module 220 may include a rules engine that defines system behavior including sensor settings, annunciations, and messages to caregivers. The algorithm module 220 may update the rules engine as new data, such as patient state and outcome, are included in the database. Updates may include weightings to neural networks, pattern matching, modified heuristics, new features such as detection of a particular physiological issue such as Cushing's Triad, and the like. Messages to caregivers may include guidance on patient care, such as suggested test intervals or statistically likely future events based on the patient's state. As described previously, the sensing patch 102 and the data processing server 106 (or more broadly the data management system 106) may communicate with each other via the bridge device 104 and the network 112. In various embodiments, processed data from the data processing server 106 may be provided to one or more users via an EHR 228, a ward dashboard 230 and/or any other suitable means for providing or displaying information. The sensor module 218 of the data processing server 106 may be configured to receive data from, and send data and/or commands to, the sensing patch 102 via the network 112. The network communication module 226, on the other hand, may be configured to send data to, and optionally receive data from, one or more devices 228, 230 via the network 112. Modules that include the data processing server may be combined and/or distributed across multiple computing devices.

FIG. 3 is a flow diagram, illustrating one embodiment of a physical parameter sensing method 240, focusing on the perspective of the sensing patch 102. In this embodiment of the method 240, the sensing patch 102 is set to default values for timing and rate of data acquisition and transmission 242. When the sensing patch 102 is attached to the subject S and activated, it will begin to acquire and transmit data at the set rates 244. At any point in time, the sensing patch 102 may receive a command 246 from the data processing server 106 to set one or more new rates 248 (of data acquisition and/or data transmission, for example). If such a command is received, the sensing patch 102 will adjust the rate(s) accordingly. If no command is received, the sensing patch 102 will continue to acquire and transmit data at the set rates 244. The set data rates 244 may include, for example, the sampling rate, such as sampling the optical detector at 250 Hz and the vital-signs interval, or acquiring vital signs every 8 hours, every 2 hours, every 10 minutes, or continuously. Logic for modifying data rates, data acquired, and the like may be included in the sensing patch 102. This supports operation when the network connection to a server is missing, and the sensing patch 102 may store data until it is read, for example, by the bridge device 104.

FIG. 4 is another flow diagram, illustrating a different portion of one embodiment of a physical parameter sensing method 250, focusing on the perspective of the data processing server 106. In this embodiment of the method 250, the sensing patch 102 acquires sensor data 252 and transmits it to the data processing server 106, which then processes the data 254. The processing step 254 may include determining the data acquisition and/or transmitting rates of the sensing patch 102. The data processing server 106 may then determine whether the data rates and data types are appropriate 256. Data types may include, for example, the sources of the data, such as sensor type, e.g., ECG, and the transmitted output, e.g., raw waveform, heart rate, R-R interval, bits per sample, or performance metric. A performance metric might include the wireless retry rate, the signal-to-noise (SNR) ratio of the communication channel, and the SNR of the data channel. If the data rates and data types are appropriate, the data processing server 106 will not send a change command to the sensing patch 102. If, however, the data processing server 106 determines that the rates and/or data types are not appropriate, then it will determine one or more changes to make to the rates and/or the data types, based on any of a number of factors. For example, the factors may include but are not limited to an acuity of the subject, an age of the subject, an instruction from a healthcare worker, a battery level of the sensing patch, an energy cost of transmitting data from the sensing patch to the processor, a noise level, a link rate for linking the sensing patch with the processor and a link reliability for linking the sensing patch with the processor, and proximity of a clinician to the sensor. At the limit of no reliability, the sensing patch 102 may automatically provide an increased amount of data reduction since there is no other processor available. Instruction from a healthcare worker may come through a user interface to the sensing patch 102 or an external computing device, including an EHR/EMR system. Proximity of a clinician may be used to indicate a clinician, who requires updated vital sign measurements, is in the room, and this information may result in commands to support the clinician's need. Any changes may then be sent in the form of commands 260 to the sensing patch 102. The sensing patch 102 may react to the command by transmitting an ACK/NACK (acknowledging/negative acknowledge) signal and/or by implementing the command.

In any embodiment of the system and method just described, the sensing patch 102 may be configured to sense multiple different physical assessment parameters and/or multiple different sensing patches 102 may be used at the same time on the same patient. In some embodiments, therefore, the data processing server 106 may be configured to receive multiple different types of data relating to different physical assessment parameters and determine whether the data rates are appropriate for any or all of those parameters, which may help improve the reliability of the received data. Again, these different parameters may be sensed by one multi-parameter sensing patch 102 or by multiple sensing patches 102. Furthermore, the methods described in FIGS. 3 and 4 may be performed continuously or at set time intervals, according to various embodiments. Changes to the data acquisition rate and/or data transmission rate may be made dynamically over a period of time. In some embodiments, the system may select to use an energy efficient sensor for heart rate, while using a less efficient sensor as needed. Multi-sensor processing may be used to leverage data from multiple sensors to improve the overall robustness of the data. For example, if ECG and SPO2 are both available, each may be used to derive a heart rate. Analyzing the heart rate (for example a sudden change) and the noise levels allows the system to determine the more reliable sensor and use that one for input. An accelerometer may be used to help determine when a sensor has motion artifact and also to remove the effects of the motion.

For example, in one embodiment, a sternal-mounted sensing patch 102 may support SPO2 (oxygen saturation), ECG, an accelerometer and an imager that determines skin color. These four measures may all be used to derive a respiration rate, and all but the imager may be used to determine a heart rate. When system values change, the data processing server 106 may analyze the cost and determine if adjustments should be made. For example, if heart rate (HR) has been stable at 80 beats per minute (BPM) and changes to 110 BPM, the data processing server 106 may change the sample period from every hour to every 10 minutes for all variables, even though the HR of 110 BPM is below the alarm limit of 120. This allows the system 100 to be more sensitive and have a shorter time lag from the onset of clinical issues to detection and alerts. The system may determine from user input or from analysis of clinician requests for routine vitals what the standard time interval is for obtaining vital signs measurements.

In some embodiments, the sensing patch 102 may perform no processing whatsoever and may simply sense one or more parameters and transmit raw data to the bridge device 104 and thus on to the data processing server 106. In that type of embodiment, the data processing server 106 may perform all data processing, or alternatively the bridge device 104 may perform some initial processing, and the data processing server 106 may perform additional processing. In that type of embodiment, the bridge device 104 may have a processor that can support applications including analysis and reduction of sensor data. This may be done fully or in part (distributed processing). For example, the bridge device 104 may compute one key numeric value, such as heart rate and use the HR data to make decisions, such as whether or not to forward the entire data packet to the data processing server 106 or to change the data sampling rate of the sensing patch 102. Alternately, the bridge device 104 may simply forward the data to the data processing server 106. The protocol might have the radio transmitting the raw data for one parameter at a time, and for each parameter the bridge device 104 or the data processing server 106 computes a numeric value and determines if the raw data for the other parameters should be immediately acquired. When a sensing patch 102 has no ability to uplink data, it may run some elementary processing, such as determining heart rate from ECG signals. In another alternative embodiment, the sensing patch 102 may perform some initial processing, such as filtering, and the data processing server 106 (and in some cases the bridge device 104) may perform additional processing. In some embodiments, the sensing patch 102 or any part of the system 100 may send reduced data. For example, the sensing patch 102 may send some waveform snippets and all the beat-to-beat intervals for heart rate variability analysis.

Figure 5:
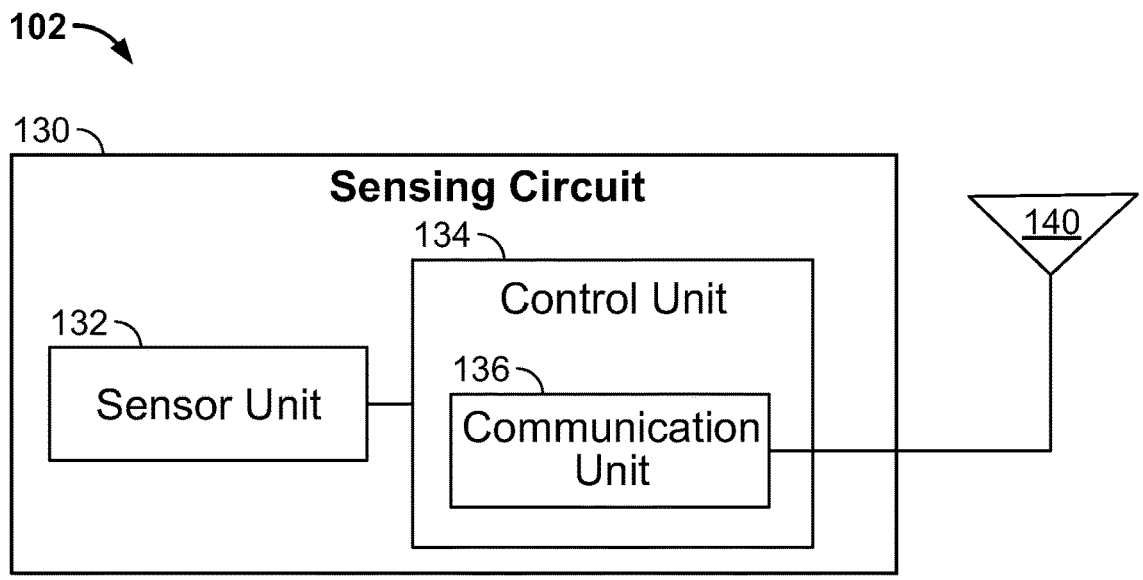
FIG. 5 schematically illustrates an example sensing device for sensing and transmitting physical assessment parameters.

FIG. 5 schematically illustrates an example of the sensing device 102, which is used for sensing and transmitting physical assessment parameters of the subject S. The sensing device 102 includes a sensing circuit 130 and an antenna 140. The sensing circuit 130 can include a sensor unit 132, a control unit 134, and a communication unit 136. The control unit 134 and the sensor unit 132 may include a processor, memory, and peripheral interfaces.

In some embodiments, the sensing device 102 operates as a transponder configured to emit an identifying signal in response to an interrogating received signal. In the depicted example, the sensing device 102 is primarily illustrated as a near field communication (NFC) unit. In other embodiments, the sensing device 102 can be designed to be in other types of communication, such as radio frequency identification (RFID) unit, Bluetooth, Wi-Fi, and other short-range wireless communications.

Figure 7:
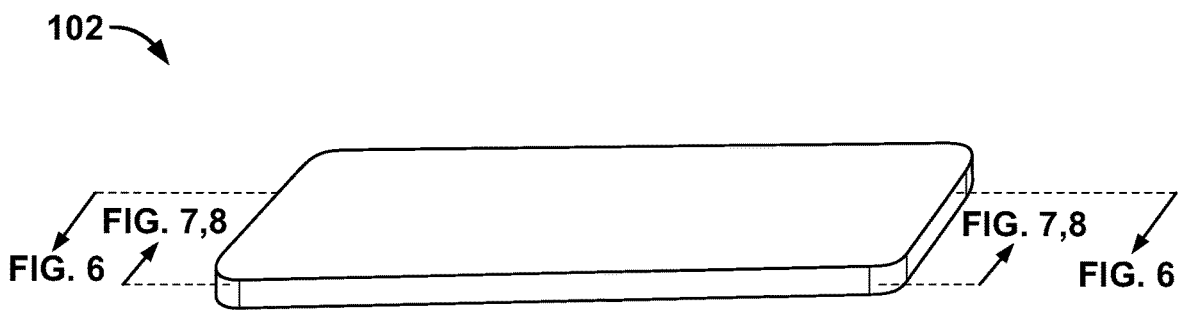
FIG. 7 is a schematic perspective view of the sensing device of FIG. 5.
Figure 8:
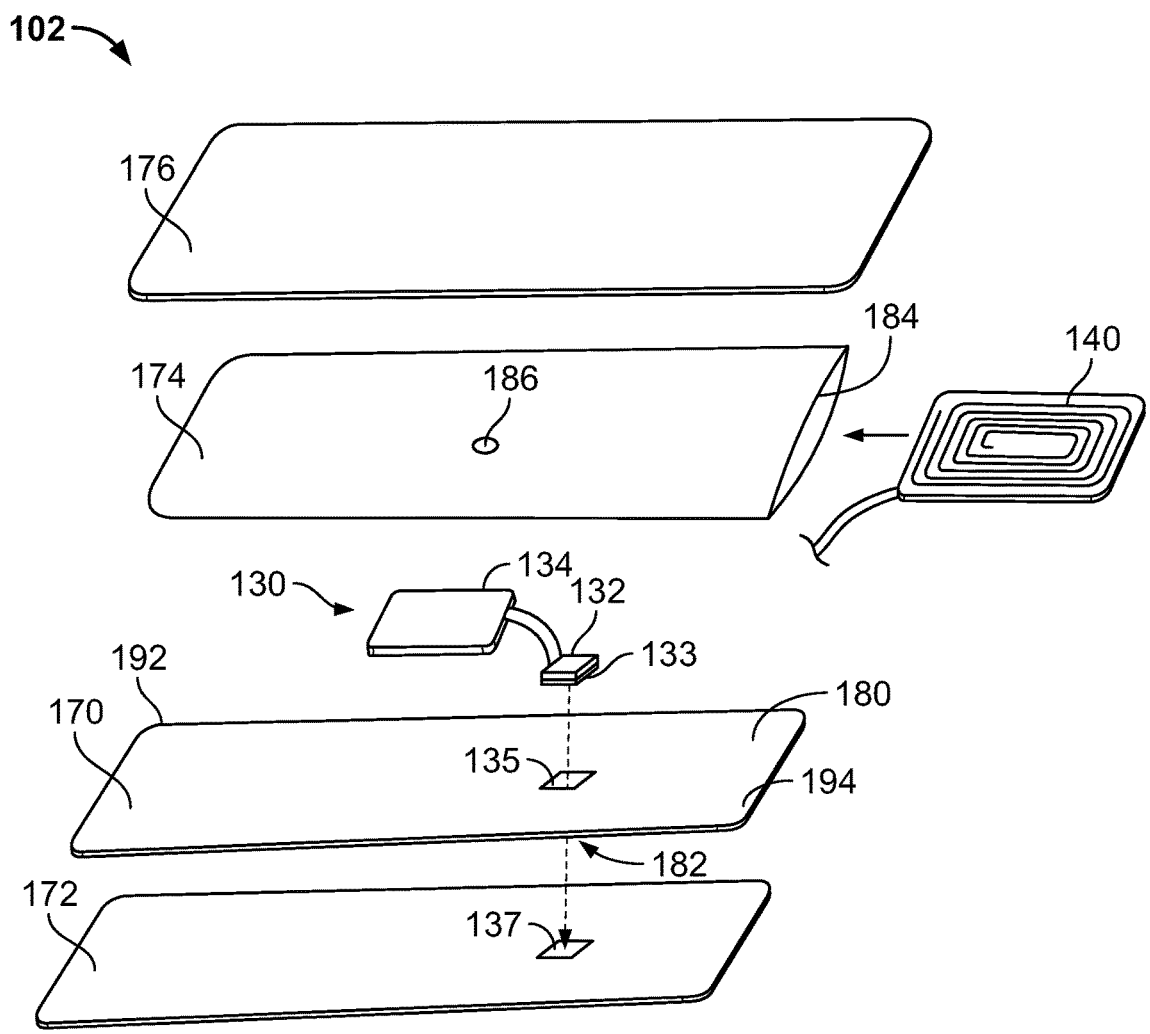
FIG. 8 schematically illustrates example components and layers of the sensing device of FIG. 7.
Figure 9:
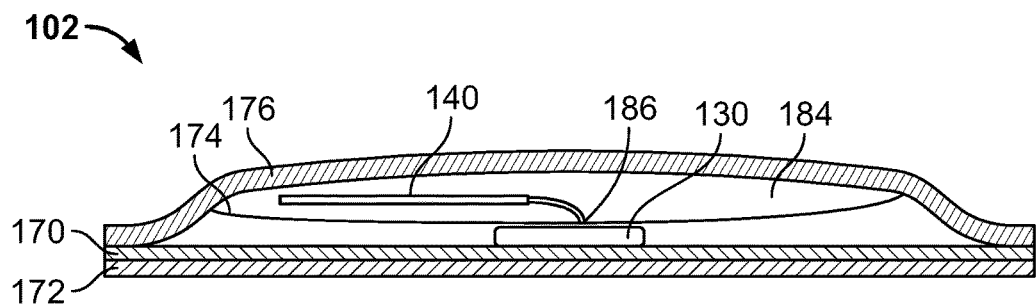
FIG. 9 is a schematic cross-sectional view of the sensing device of FIG. 7.

As further illustrated in FIGS. 7-9, the sensing device 102 can be configured as a patch. The sensing circuit 130 can be designed as a tag or label suitable to be contained within the patch. The tag or label can be formed to be substantially flat and thin so as to be easily mounted onto, or embedded into, the patch.

The sensor unit 132 includes one or more sensors operable to detect one or more physical assessment parameters. In some examples, the sensor unit 132 includes one sensor for detecting one type of physical assessment parameters. In other examples, the sensor unit 132 includes multiple sensors for detecting different types of physical assessment parameters. Example sensors of the sensor unit 132 include temperature sensors, heartrate sensors, electrocardiogram (ECG) sensors, respiratory rate sensors, accelerometers, SpO2 sensors, heart rate variability sensors, galvanic skin response sensors, blood pressure sensors, blood chemistry sensors, including blood glucose sensors, blood oxygen sensors, and any other sensors suitable for measuring physical assessment parameters. The sensor unit 132 can further include one or more sensors (e.g., accelerometer) for detecting the subject's activity and posture, such as whether the subject is standing, sitting, laying down, or engaged in physical activity, such as running.

The control unit 134 operates to process signals obtained by the sensor unit 132. Data processed by the control unit 134 can be stored in a storage unit. An example of the control unit 134 is further described with reference to FIG. 6.

The communication unit 136 operates to send signals obtained by the sensor unit 132 to the bridge device 104 via the wireless communication link 110. In some examples, the communication unit 136 can also receive signals from the bridge device 104. In some examples, the communication unit 136 is configured to communicate with the data management system 106 and/or other computing devices via the network 112. Although the communication unit 136 is illustrated to be included in the control unit 134, the communication unit 136 can be configured separately from the control unit 134.

The antenna 140 is configured to receive and transmit a radio frequency (RF) signal. In some embodiments, the antenna 140 is configured for NFC communication. The communication range for NFC communication is generally proportional to the size of the antenna. Therefore, it may be desirable to increase the antenna size to increase the reading range of a patient worn sensor (e.g., the sensing patch 102).

In some embodiments, the antenna 140 is made flat so as to be incorporated into the sensing patch 102 as illustrated in FIGS. 7-9. In the illustrated example, the antenna 140 is separate from the sensing circuit 130. Since the antenna 140 need not be formed together with the sensing circuit 130 on a single printed circuit board, the sensing circuit 130 can be made smaller, thereby improving comfort when the sensing patch 102 is attached on the subject's body skin. As described above, the sensing circuit 130 includes the sensor unit 132 that can be separated from the processing unit circuit board (e.g., the control unit 134) such that only the sensor unit 132 contacts the body skin. Since the critical skin contact is limited to the sensor unit, the skin contact area required is further reduced. In other embodiments, the antenna 140 can be formed on the sensing circuit 130. An example of the antenna 140 is described and illustrated in more detail with reference to FIGS. 7-11.

Figure 6:
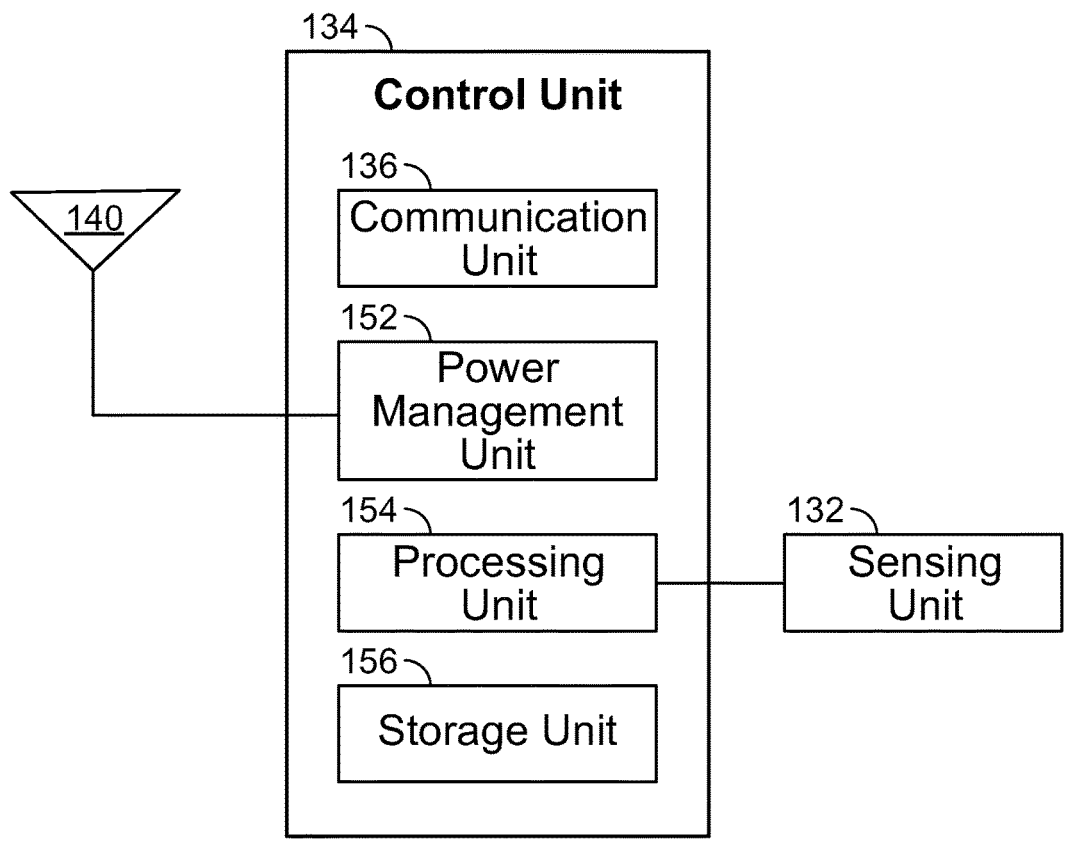
FIG. 6 schematically illustrates an example control unit of the sensing device of FIG. 5.

FIG. 6 schematically illustrates an example of the control unit 134 of FIG. 5. In the illustrated example, the control unit 134 is configured for NFC or RFID communication.

The control unit 134 is arranged within the sensing patch 102 and electrically coupled to the antenna 140. In some embodiments, the control unit 134 is implemented in an integrated circuit (IC). In operation, a signal is received by the antenna 140 and communicated to the control unit 134. The control unit 134 operates to harvest power and respond as necessary in response to the incoming signal. In particular, the control unit 134 is configured to store and process information, modulate and demodulate a RF signal, collect power from an associated reader signal, and perform other functions. One example of the control unit 134 is implemented with model number RF430FRL152H, available from Texas Instruments Inc., Dallas, Tex.

In some embodiments, the control unit 134 includes a power management unit (PMU) 152, a processing unit 154, and a storage unit 156. In other embodiments, the control unit 134 can include one or more components in addition to the components described above, and/or replace one or more of the components described above by different components.

The PMU 152 operates to harvest raw RF power received via the antenna 140. In particular, an RF wave received via the antenna 140 is transmitted to the PMU 152 as a signal. The signal is used for harvesting the power and also decoded for further processes. Where the sensing patch 102 is implemented as a passive NFC device, the sensing patch 102 does not have its own power source. The sensing patch 102 can be powered by electromagnetic induction from magnetic fields produced near a reader of the sensing patch 102 (e.g., the bridge device 104). However, it is recognized that the control unit 134 can be powered in different manners. For example, where the sensing patch 102 is implemented as an active or semi-passive RFID tag, the sensing patch 102 uses internal power source to power the circuit.

The processing unit 154 operates to receive signals from the antenna 140. In some examples, a demodulator is provided to demodulate an RF signal received via the antenna 140. The demodulator can be implemented in a way known in the art, including, for example, attenuator stage and amplifier stage. The processing unit 154 can perform various operations and generate an output signal for transmission. In some examples, a modulator is provided to modulate an output signal generated by the processing unit 154. The modulated signal is transmitted through the antenna 140 to one or more readers, such as the bridge device 104. The modulator can be implemented in a way known in the art, including, for example, driver stage and amplifier stage. The processing unit 228 can be implemented in a way known in the art, including, for example, a processor, a decoder, and an encoder. In another example, the control unit 134 modulates the load as a function of the data bit stream, e.g., binary amplitude modulation may be achieved by applying more load for a 1 and less load for a 0. The reader can detect the power transfer using transformer theory and thereby determine the data bit stream. An analog output of the sensor unit could provide direct modulation of the signal transmitted by the communication unit.

The storage unit 156 includes one or more memories configured to store data readable by a reader, such as the bridge device 104. The storage unit 156 can be of various types, including volatile and nonvolatile, removable and non-removable, and/or persistent media. In some embodiments, the storage unit 156 is an erasable programmable read only memory (EPROM) or FLASH memory.

Referring to FIGS. 7-9, an example structure of the sensing device 102 is described. In particular, FIG. 7 is a schematic perspective view of the sensing device 102. FIG. 8 schematically illustrates example components and layers of the sensing patch 102 of FIG. 7, and FIG. 9 is a schematic cross-sectional view of the sensing patch 102 of FIG. 7.

As illustrated, the sensing device 102 is configured as a patch that can be removably attached to various portions of the subject's body. In some examples, the sensing patch 102 includes a base substrate or layer 170, an adhesive layer 172, an antenna enclosure 174, and a cover layer 176. As described below, the antenna 140 is movably contained within the sensing patch 102, thereby improving the flexibility of the sensing patch 102 that is attached on the subject's body skin.

Referring to FIGS. 8 and 9, the base substrate 170 has a first surface 180 supporting the sensing circuit 130 thereon, and a second surface 182 (opposite to the first surface) configured to, directly or indirectly, engage a portion of the subject's body (e.g., body surface). In some examples, the adhesive layer 172 is provided on the second surface 182 of the base substrate 170 to allow the base substrate 170 (and thus the patch 102) to be attached to a body surface of the subject S. In other examples, the second surface 182 of the base substrate 170 is adapted to be removably attached to a body surface of the subject S with or without the adhesive layer 172. In some examples, the base substrate 170 is made of flexible materials, such as polymeric materials, which are stretchable to remain attached to a body skin when the body skin deforms.

The adhesive layer 172 can be made of various materials. In some examples, the adhesive layer 172 is made of flexible polymeric materials, which are stretchable to conform to the deformation of a body skin on which the sensing patch 102 is attached. The adhesive layer 172 can include a hydrogel, which can provide skin-adhesion properties. The adhesive layer 172 can further function as a thermal conduit between the sensor unit 132 and the subject's skin. In addition or alternatively, the adhesive layer 172 includes a pressure-sensitive adhesive.

In addition or alternatively, the adhesive layer 172 is further configured as an electrically conductive layer that can conduct current between the skin and the circuit. Further, such an electrically conductive layer can also transfer a measurement of a voltage potential between two different points on the patient to the sensing circuit.

In some examples, the base substrate 170 is configured such that the entire second surface 182 of the base substrate 170 is substantially attached to a predetermined body skin of the subject S, either directly or through the adhesive layer 172. In other examples, the base substrate 170 is configured to be attached to a body skin at a limited number of points of the second surface 182 of the base substrate 170 (either directly or via the adhesive layer 172). For example, in the illustrate example, the base substrate 170 can be attached to a body skin at two points adjacent opposite corners 192 and 194 (FIG. 8). This configuration can be used in measuring a stretch of a skin, which, for example, can be used to calculate a breath rate.

In some examples, the sensing circuit 130 is disposed between the base substrate 170 and the antenna enclosure 174. The sensing circuit 130 can be attached to the base substrate 170. For examples, the control unit 134 is fixed to a predetermined location on the first surface 180 of the base substrate 170, and the sensor unit 132 is arranged at a location from which a desired physical assessment parameter can be properly detected when the patch 120 is attached to the subject S. Alternatively, the sensing circuit 130 can be attached to the antenna enclosure 174, or attached to both the base substrate 170 and the antenna enclosure 174. In this example, the sensor unit 132 is illustrated to be separate and extend from the control unit 134. In other examples, the sensor unit 132 can be incorporated with the control unit 134 as a single printed circuit board.

In some embodiments, the sensor unit 132 includes a sensor adhesive layer 133 configured to attach the sensor unit 132 to the subject's skin. The sensor unit 132 can be exposed to the skin through an opening 135 of the base substrate 170 and an opening 137 of the adhesive layer 172.

Where the sensing patch 102 is configured for measuring a body temperature, the sensor unit 132 can include a thermistor or multiple thermistors in some examples. In other examples, the sensor unit 132 can include other types of electrical temperature sensors, including thermocouples, diodes, and other semiconductors.

The antenna enclosure 174 is configured to house the antenna 140 therewithin. The antenna enclosure 174 provides a space or cavity 184 within which the antenna 140 can move. In some examples, the antenna enclosure 174 is configured as a pocket, sleeve, or envelope into which the antenna 140 is received. The antenna enclosure 174 is sized such that the antenna 140 freely moves, or floats, within the antenna enclosure 174. The antenna enclosure 174 can be made from one or more flexible and stretchable materials. The antenna enclosure 174 can be made in other manners. For example, the antenna enclosure 174 can be made by two opposing layers that cooperate together to define a space therebetween. By way of example, such opposing layers can be the base substrate 170 and the cover layer 176.

In some examples, the antenna enclosure 174 includes a wire hole 186 through which electrical wires pass between the antenna 140 and the sensing circuit 130. The electrical wires are used to electrically connect the antenna 140 and the sensing circuit 130.

The cover layer 176 can be disposed above the antenna enclosure 174 and forms an exterior layer of the sensing patch 102. In some examples, the cover layer 176 and the base substrate 170 are connected (e.g., bonded) to each other along their edges to enclose the antenna enclosure 174, the sensing circuit 130, the antenna 140, and other components or layers suitable for the sensing patch 102.

The materials used for the layers of the sensing patch 102 are capable of providing resistance to water, sweat, humidity, and other human or environmental factors that may reduce or deteriorate the bond between the patch 102 and the subject's skin over the length of a predetermined time period.

In some examples, the layers of the sensing patch 102, such as the base substrate 170, the adhesive layer 172, the antenna enclosure 174, and the cover layer 176, are made to be flexible and stretchable to accommodate the movement of a body skin of the subject S to which the sensing patch 102 is attached. As such, when the body skin moves or changes its shape (e.g., the body skin stretches or shrinks), the layers of the sensing patch 102 can remain properly attached to the body skin by conforming to the various shapes of the body skin. Since the sensing circuit 130 is small in size relative to the sensing patch 102, the sensing circuit 130 does not generally interfere with the flexibility of the layers of the sensing patch 102. In other examples, the sensing circuit 130 can also be made with a flexible circuit board so that the layers and the sensing circuit 130 of the sensing patch 102 conform to different shapes of the subject's body skin on which the sensing patch 102 is attached.

In other examples, the sensing patch 102 can include other layers and/or components in addition to all or some of the layers 170, 172, 174 and 176. Further, the layers and components of the sensing patch 102, such as the base substrate 170, the adhesive layer 172, the antenna enclosure 174, the cover layer 176, the sensing circuit 130, the antenna 140, and/or any other layers or components, can be arranged in various manners, different from the order illustrated in FIGS. 8 and 9.

In some examples, the antenna 140 is designed to generally follow the contour of the sensing patch 102. The antenna 140 is made of one or more rigid materials, such as aluminum and copper, which is not stretchable. Where the sensing patch 102 is configured as a NFC or RFID device, the antenna 140 is made from etched metal foil. For example, the antenna 140 can include one or more coils, which are formed as a loop, a spiral, a square or rectangular, on a flat plate.

Several factors can affect a read range between the bridge device 104 and the sensing patch 102. One factor is an antenna size. In general, a larger antenna can broadcast farther than a smaller one. However, such a larger antenna interferes more with the flexibility of the sensing patch.

The non-stretchable characteristic and the relatively-large size of the antenna 140 can prevent the sensing patch 102 from confirming to deformation of a body skin and the layers of the sensing patch 102 attached to the body skin and/or restrict natural skin stretching motion. As described above, the antenna enclosure 174 can reduce the interference of the antenna 140 by allowing the antenna 140 to float, or move freely, relative to the sensing patch 102. Therefore, the existence of the antenna 140 does not deteriorate the flexibility of the sensing patch 102, which can thus conform to the deformation of a body skin on which the sensing patch 102 is attached.

Although the sensing patch 102 is made be flexible in general, the sensing patch 102 is configured to be unswallowable and/or not chewable. In some examples, the sensing patch 102 includes one or more layers or members that are at least partially rigid and can thus prevent the subject S (such as a pediatric patient) from accidentally ingesting the sensing patch 102. In other examples, the sensing patch 102 is sized to be large enough so that a pediatric patient is not able to swallow the sensing patch 102. In yet other examples, the sensing patch is treated with a biocompatible, non-toxic coating that has an undesirable taste or flavor to prevent the subject from swallowing or ingesting the patch.

Similarly to the antenna 140 above, in some examples, the sensing circuit 130 can be movably contained within the sensing patch 102. For example, the sensing circuit 130 can be received within the antenna enclosure 174 so that the sensing circuit 130, as well as the antenna 140, freely moves within the antenna enclosure 174. In other examples, another enclosure, similar to the antenna enclosure 174, can be provided to provide a space for the movement of the sensing circuit 130. For reliable measurement, the sensor unit 132 can be fixed within the sensing patch 102 while the control unit 134 of the sensing circuit 130 and/or the antenna 140 are movably disposed within the sensing patch 102.

Figure 10:
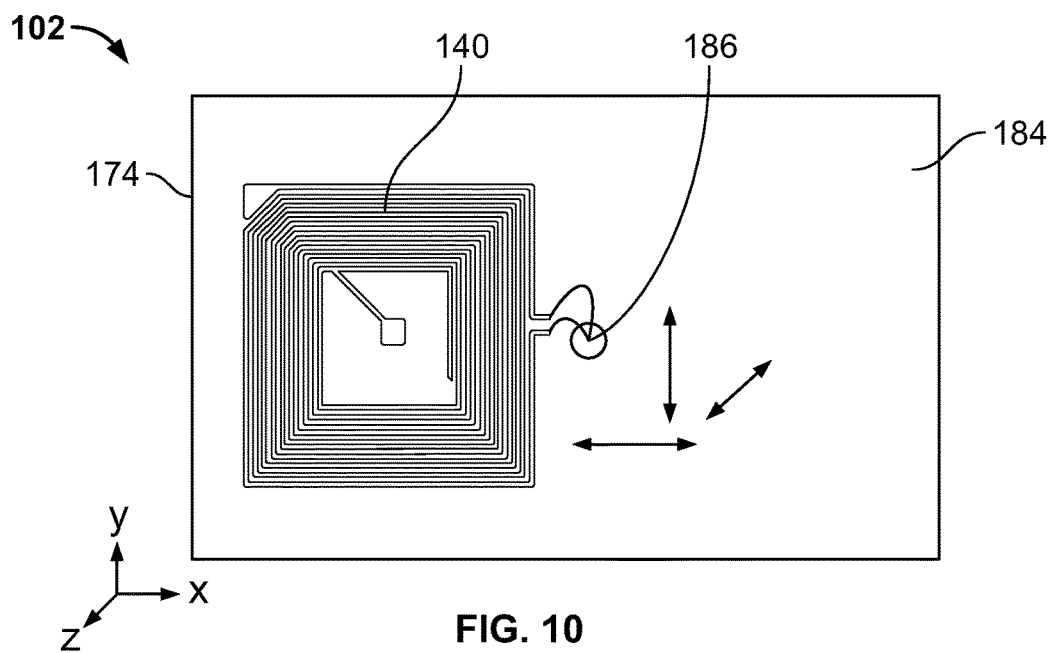
FIG. 10 schematically illustrates an example antenna arrangement within an antenna enclosure of the sensing device.
Figure 11:
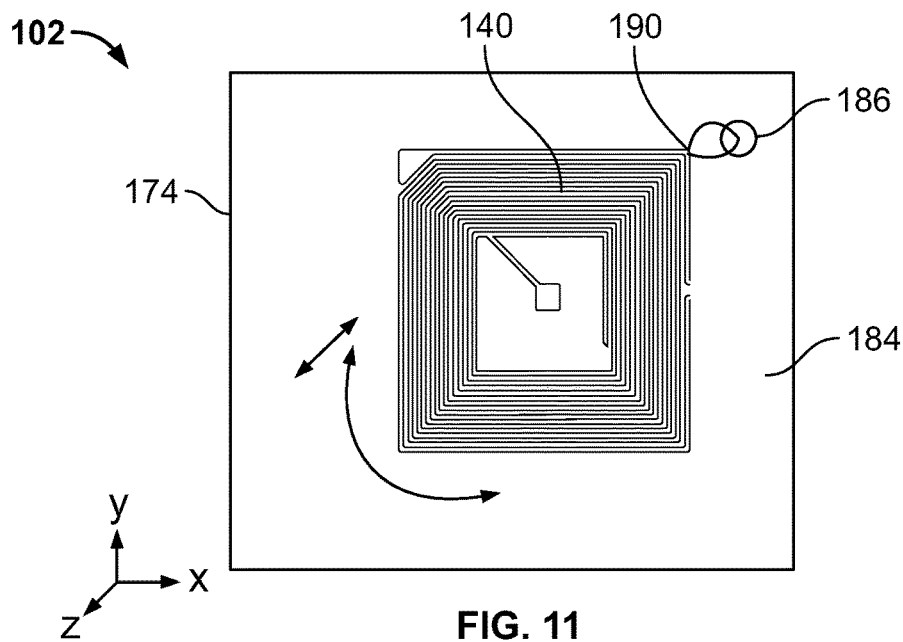
FIG. 11 schematically illustrates another example antenna arrangement within the antenna enclosure of the sensing device.

Referring to FIGS. 10 and 11, the antenna 140 is described to be disposed within the antenna enclosure 174 in various manners. In particular, FIG. 10 schematically illustrates an example arrangement of the antenna 140 within the antenna enclosure 174, and FIG. 11 schematically illustrates another example arrangement of the antenna 140 within the antenna enclosure 174.

With reference to FIG. 10, the antenna 140 is disposed within the antenna enclosure 174 and movable therewithin. The movement of the antenna 140 is only limited by the wires extending from the antenna 140 to the sensing circuit 130 through the wire hole 186. The antenna 140 can freely move in the three-dimensional space of the cavity 184 (e.g., a space defined by three-dimensional Cartesian coordinate system).

With reference to FIG. 11, the antenna 140 can be disposed within the antenna enclosure 174 and pivotally connected at a predetermined anchor point 190. In this configuration, the antenna 140 can pivot about the anchor point 190 on the x-y plane and movable along the z-axis.

The antenna 140 can be fixed at a single point, such as the anchor point 190, and the rest of the antenna 140 is not fixed relative to the subject's skin on which the sensing patch 102 is attached. Therefore, the antenna 140 is allowed to move or slide within the antenna enclosure 174. As such, the sensing patch 102 is not restrained by the rigid antenna 140 and is adapted to be stretchable in response to the deformation (e.g., stretching or shrinking) of the subject's skin. In other examples, the antenna 140 can be fixed at two or more points within the antenna enclosure 174 while the antenna 140 is sufficiently movable within the antenna enclosure 174 as the sensing patch 102 and/or the subject's skin deform.

Figure 12:
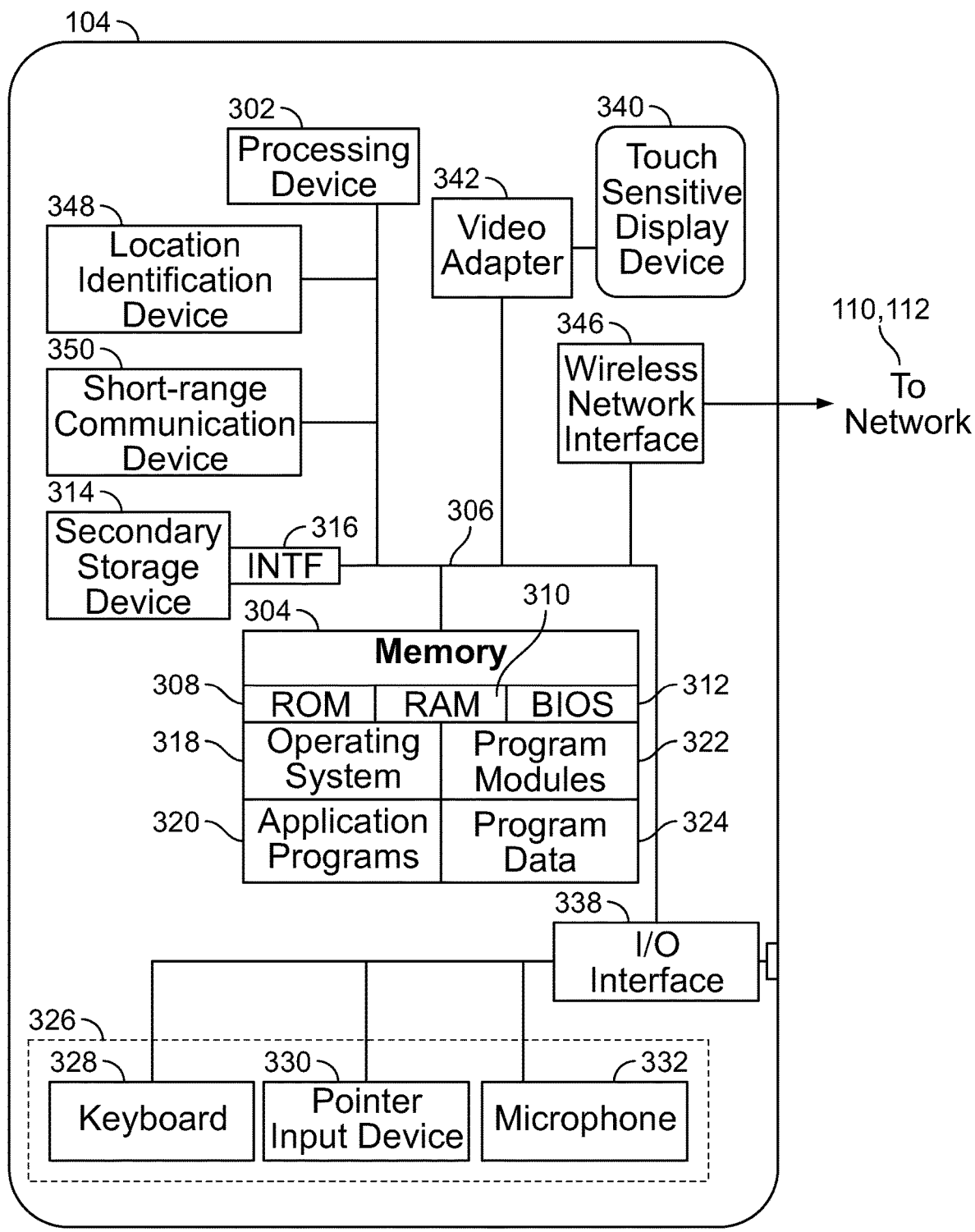
FIG. 12 illustrates an exemplary architecture of a reading device of the system of FIG. 1.

FIG. 12 illustrates an exemplary architecture of the bridge device 104. The bridge device 104 illustrated in FIG. 12 is used to execute the operating system, application programs, and software modules (including the software engines) described herein.

The bridge device 104 is a computing device of various types. In some embodiments, the bridge device 104 is a mobile computing device. Examples of the bridge device 104 as a mobile computing device include a mobile device (e.g., a smart phone and a tablet computer), a wearable computer (e.g., a smartwatch and a head-mounted display), a personal digital assistant (PDA), a handheld game console, a portable media player, an ultra-mobile PC, a digital still camera, a digital video camera, and other mobile devices. In other embodiments, the bridge device 104 is other computing devices, such as a desktop computer, a laptop computer, or other devices configured to process digital instructions.

It is recognized that the architecture illustrated in FIG. 12 can also be implemented in other computing devices used to achieve aspects of the present disclosure. For example, the data management system 106 can be configured similarly to the architecture of FIG. 12. To avoid undue repetition, this description of the bridge device 104 will not be separately repeated herein for each of the other computing devices including the data management system 106.

The bridge device 104 includes, in some embodiments, at least one processing device 302, such as a central processing unit (CPU). A variety of processing devices are available from a variety of manufacturers, for example, Intel or Advanced Micro Devices. In this example, the bridge device 104 also includes a system memory 304, and a system bus 306 that couples various system components including the system memory 304 to the processing device 302. The system bus 306 is one of any number of types of bus structures including a memory bus, or memory controller; a peripheral bus; and a local bus using any of a variety of bus architectures.

The system memory 304 includes non-volatile memory 308 and random access memory 310. A basic input/output system 312 containing the basic routines that act to transfer information within the bridge device 104, such as during start up, is typically stored in the non-volatile memory 308.

The bridge device 104 also includes a secondary storage device 314 in some embodiments, such as a hard disk drive, for storing digital data. The secondary storage device 314 is connected to the system bus 306 by a secondary storage interface 316. The secondary storage devices and their associated computer readable media provide nonvolatile storage of computer readable instructions (including application programs and program modules), data structures, and other data for the bridge device 104.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, FLASH memories, removable memories such as USB memory sticks, or read only memories. Some embodiments include non-transitory media.

A number of program modules can be stored in secondary storage device 314 or memory 304, including an operating system 318, one or more application programs 320, other program modules 322, and program data 324.

In some embodiments, the bridge device 104 includes input devices to enable a user to provide inputs to the bridge device 104. Examples of input devices 326 include a keyboard 328, a pointer input device 330, a microphone 332, and a touch sensitive display 340. Other embodiments include other input devices. The input devices are often connected to the processing device 302 through an input/output interface 338 that is coupled to the system bus 306. These input devices 326 can be connected by any number of input/output interfaces, such as a parallel port, serial port, game port, or a universal serial bus. Wireless communication between input devices and interface 338 is possible as well, and includes infrared, BLUETOOTH® wireless technology, 802.11a/b/g/n/ac/ad, cellular, or other radio frequency communication systems in some possible embodiments.

In this example embodiment, a touch sensitive display device 340 is also connected to the system bus 306 via an interface, such as a video adapter 342. The touch sensitive display device 340 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 340, the bridge device 104 can include various other peripheral devices (not shown), such as speakers or a printer.

When used in a local area networking environment or a wide area networking environment (such as the Internet), the bridge device 104 is typically connected to the network through a network interface, such as a wireless network interface 346. Other possible embodiments use other communication devices. For example, some embodiments of the bridge device 104 include an Ethernet network interface, or a modem for communicating across the network.

The bridge device 104 typically includes at least some form of computer-readable media. Computer readable media includes any available media that can be accessed by the bridge device 104. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the bridge device 104. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 12 is also an example of programmable electronics, which may include one or more such computing devices, and when multiple computing devices are included, such computing devices can be coupled together with a suitable data communication network so as to collectively perform the various functions, methods, or operations disclosed herein.

Referring again to FIG. 12, the bridge device 104 can include a location identification device 348. The location identification device 348 is configured to identify the location or geolocation of the bridge device 104. The location identification device 348 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Referring again to FIG. 12, the bridge device 104 further includes a short-range wireless communication device 350. The short-range wireless communication device 350 is configured to establish short-range wireless communication with the sensing patch 102. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A system for detecting one or more physical assessment parameters of a subject, the system comprising:
   a sensing patch configured to sense signals from the subject corresponding to the one or more physical assessment parameters, process the sensed signals into sensed parameter data, and transmit the sensed parameter data corresponding to the sensed signals, wherein the sensing patch includes at least one adjustable sensing patch parameter;
   a bridge device configured to receive the sensed parameter data from the sensing patch and transmit the sensed parameter data to another device; and
   a data processing server, separate from the sensing patch and the bridge device, the data processing server configured to receive the sensed parameter data from the bridge device and transmit a command to the sensing patch via the bridge device,
   wherein distributed processing is performed between the sensing patch, the bridge device, and the data processing server such that the sensing patch is configured to modify the at least one adjustable sensing patch parameter to perform different amounts of data reduction on the sensed signals before transmitting the sensed parameter data, wherein the data reduction includes processing the sensed signals, wherein the sensing patch automatically provides an increased amount of data reduction when the bridge device and the data processing server are not available, wherein the different amounts of data reduction are determined for each of the sensing patch, bridge device, and data processing server at least in part by at least one system parameter corresponding to a function of the system; and wherein the distributed processing includes to configure the sensing patch to transmit the sensed parameter data as raw data to the bridge device, and to configure the bridge device to compute a physical assessment parameter from the raw data and to use the physical assessment parameter to determine whether to forward additional raw data from the sensing patch to the data processing server.

2. The system of claim 1, wherein the at least one adjustable sensing patch parameter is selected from the group consisting of a data reduction rate, a rate at which the sensing patch senses signals from the subject, a monitored vital sign, a data uplink interval and a vital signs interval.

3. The system of claim 1, wherein the different amounts of data reduction are further determined, at least in part, by a state of the subject.

4. The system of claim 1, wherein the at least one system parameter is selected from the group consisting of a battery level of the sensing patch, an energy cost of transmitting sensed parameter data from the sensing patch to the bridge device, a noise level, a link rate for linking the sensing patch with the bridge device and a link reliability for linking the sensing patch with the bridge device.

5. The system of claim 1, wherein the command transmitted from the data processing server to the sensing patch comprises an amount of data reduction to be performed by the sensing patch, and wherein the sensing patch is configured to receive and react to the command.

6. The system of claim 1, wherein the system receives one or more inputs for determining the different amounts of the data reduction performed by the sensing patch, the bridge device, and the data processing server.

7. The system of claim 6, wherein the one or more inputs include patient acuity, battery level, energy cost to transmit data, link rate, and link reliability.

8. The system of claim 1, wherein the sensing patch is a multi-parameter wearable sensor.

9. The system of claim 1, wherein the distributed processing is performed between the bridge device and the data processing server.

10. The system of claim 1, wherein the data processing server performs all of the processing of the sensed signals.

11. The system of claim 1, wherein the bridge device computes another physical assessment parameter from the sensed signals and uses the another physical assessment parameter to determine whether to change a data sampling rate of the sensing patch.

* * * * *